United States Patent [19]

Bujan

[11] 4,381,005
[45] Apr. 26, 1983

[54] INTRAVENOUS PUMP CHAMBER
[75] Inventor: Albert F. Bujan, Waukegan, Ill.
[73] Assignee: Abbott Laboratories, North Chicago, Ill.
[21] Appl. No.: 278,546
[22] Filed: Jun. 29, 1981
[51] Int. Cl.³ .................. A61M 5/00; F09B 21/02
[52] U.S. Cl. ............................ 604/152; 417/566
[58] Field of Search ............ 128/214, 214 E, 214 F, 128/DIG. 12; 417/566, 559, 569, 571

[56] References Cited
U.S. PATENT DOCUMENTS
3,354,830 11/1967 Mortara ..................... 417/566 X
3,620,650 11/1971 Shaw ........................... 128/214 E
3,976,402 8/1976 Lundquist ................... 417/566

Primary Examiner—Stephen C. Pellegrino
Attorney, Agent, or Firm—Robert L. Niblack; Neil E. Hamilton

[57] ABSTRACT

A disposable intravenous pump chamber cassette for an intravenous administration set which is specifically fabricated for use with the administration of blood. The pump chamber is specifically constructed to be utilized in conjunction with an intravenous pump having a driver to activate a diaphragm member and includes an improved outlet valve member having an outwardly extending lateral wall surface to direct the blood away from the biasing mechanism for the outlet valve member to thereby substantially reduce hemolysis.

10 Claims, 3 Drawing Figures

INTRAVENOUS PUMP CHAMBER

BACKGROUND OF THE INVENTION

This invention relates to a pump chamber for an intravenous or blood pump of the positive displacement type. More particularly, this invention relates to a pump chamber cassette for an intravenous pump wherein a diaphragm is moved inwardly by a driver element to force blood out of a cavity and through a biased outlet valve which is designed to substantially reduce blood hemolysis.

The pump chamber of this invention is fabricated to be employed in a pumping device of the type described in U.S. Pat. No. 3,620,650. The basic pump cassette of which this cassette is an improvement is currently being marketed by Abbott Laboratories of North Chicago, Ill. in an I.V. pump under the name Abbott/Shaw Life Care Pump. Some problems have been encountered in utilizing the currently marketed cassette in connection with the pumping of blood. As indicated in U.S. Pat. No. 3,620,650, a biased outlet valve is employed with a biasing means in the form of an exposed spring. The same is true of the unit being marketed currently which employs a ball with the spring. When blood is pumped through the biased ball outlet valve having an exposed spring member, high shear pressure is effected because of the geometric configuration of the valve seat and valve member and the spring which is exposed to fluid flow. When packed red cells are administered through the current cassette, the shear velocity and contact with the spring causes excess hemolysis of the cells.

It is an advantage of the present invention to provide a novel pump chamber cassette for an I.V. positive displacement pump useful for administering blood. Other advantages are a pump chamber for a blood administration set pump which substantially reduces hemolysis during administration; a unique biased outlet valve member in the outlet passage of the pump chamber cassette; a pump cassette which can be manufactured at low cost so as to not add an appreciable amount of cost to an intravenous adminstration set, yet can administer I.V. solutions as well as blood.

SUMMARY OF THE INVENTION

The foregoing advantages are accomplished and the shortcomings of the prior art are overcome by the present pump chamber cassette for a positive displacement pump wherein the pump chamber has a housing member presenting a cavity portion. Inlet and outlet passage means are in fluid communication with the cavity with a one-way valve means positioned in the inlet passage. A diaphragm member is positioned over the cavity and spaced from the outlet passage. A plunger member is slidably positioned to contact the diaphragm with the plunger being driven by a driver means opposite the diaphragm. The outlet passage includes a valve seat and an outlet valve member. Biasing means is positioned with respect to the valve member to bias it against the valve seat in an axial manner. The outlet valve member has an outwardly extending lateral wall surface formed in a manner to direct liquid away from the biasing means as the liquid passes through the outlet passage. In a preferred manner, the biasing means is a spring member and the valve member includes a stem portion to receive the spring. The valve member has a substantially flat end surface positioned opposite the biasing means and includes a rounded shoulder portion for contact with the valve seat. The valve seat is constructed with an annular passageway which progressively increases in the direction of liquid flow.

BRIEF DESCRIPTION OF THE DRAWINGS

A better understanding of the intravenous pump chamber cassette will be accomplished by reference to the drawings wherein.

DESCRIPTION OF THE INVENTION

Figure 1:
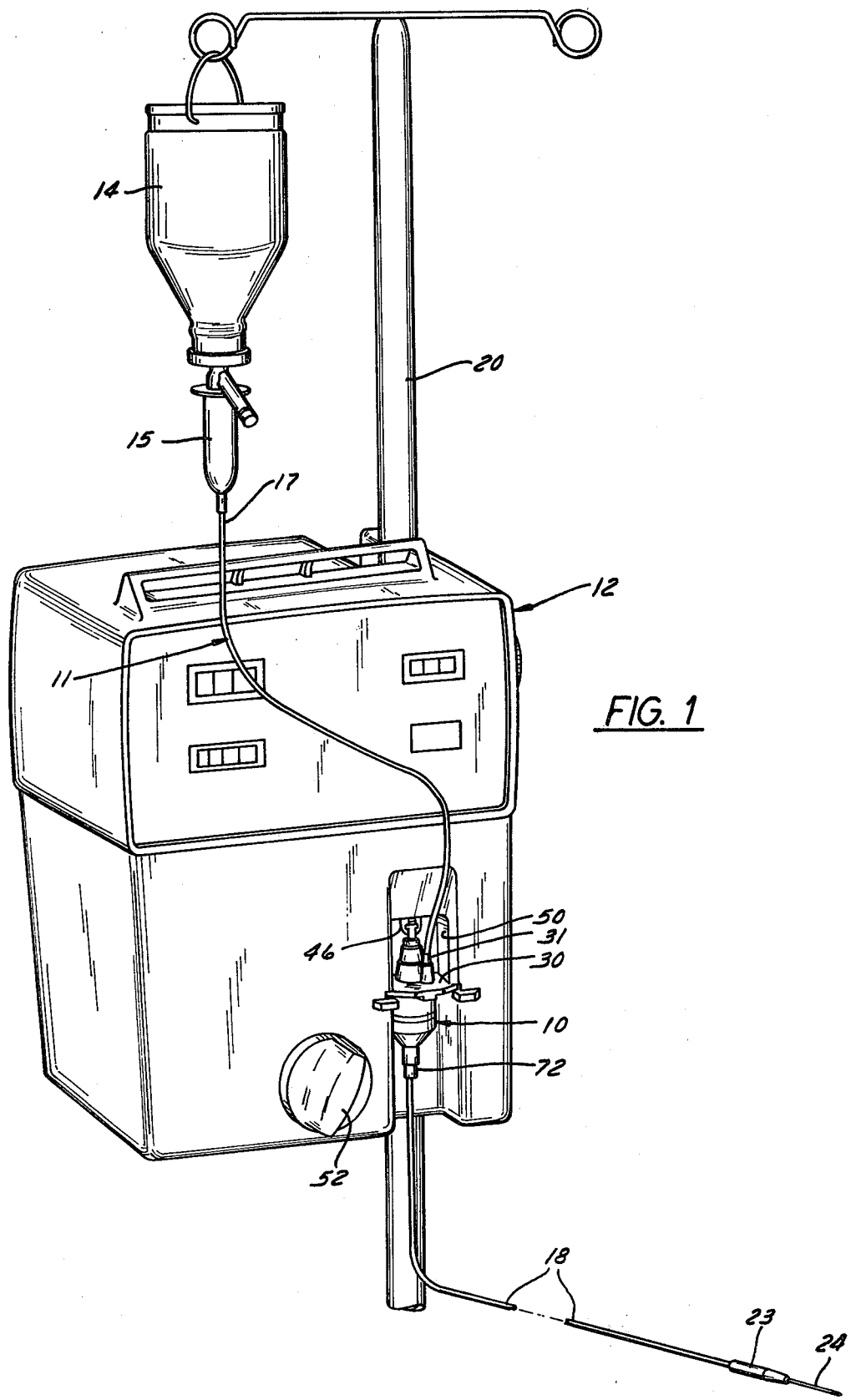
FIG. 1 is a perspective view of an intravenous administration set with an I.V. pump of the type in which the pump chamber cassette of this invention would be utilized.
Figure 2:
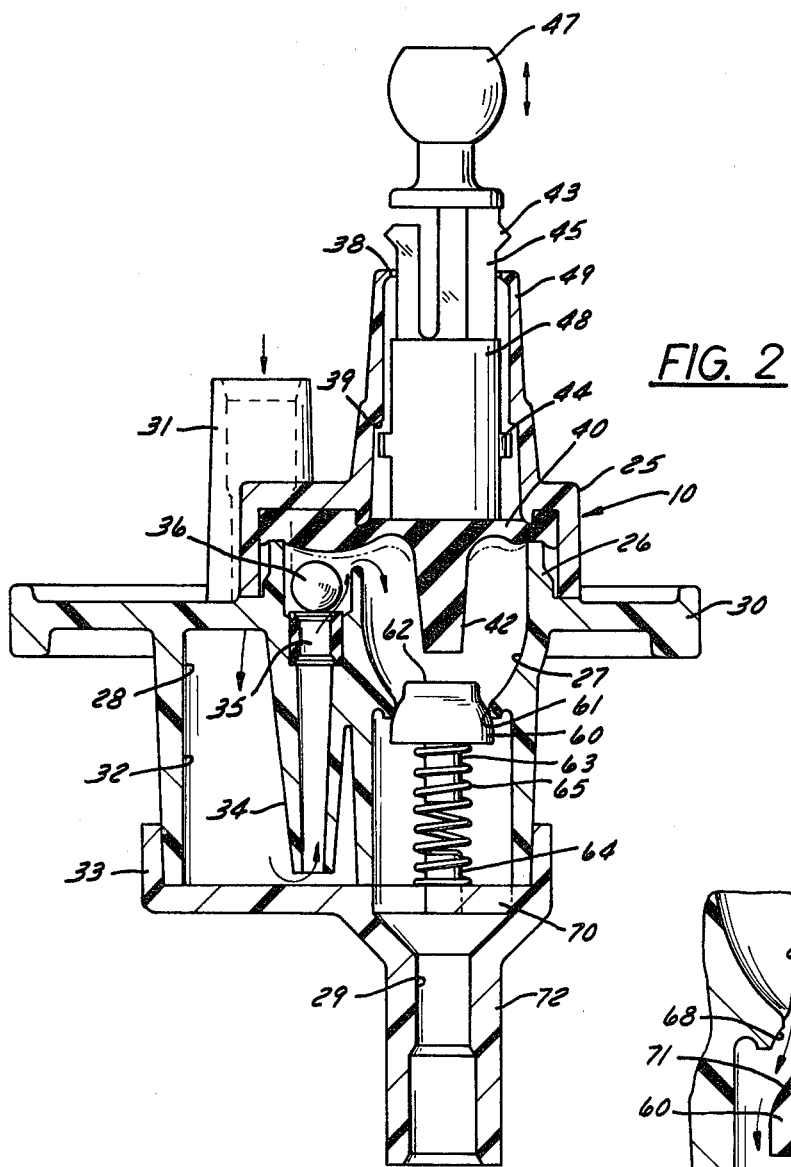
FIG. 2 is an enlarged view in vertical section showing the pump chamber cassette of this invention and with the outlet valve in the closed position.
Figure 3:
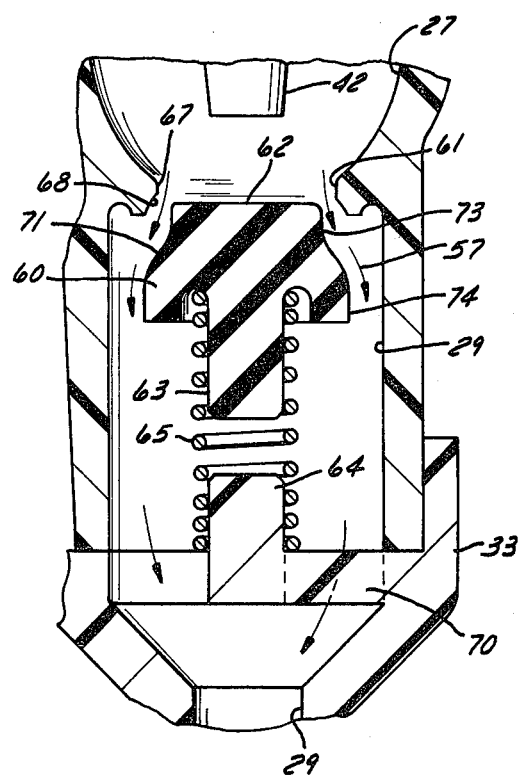
FIG. 3 is an enlarged partial view in vertical section of the pump chamber cassette shown in FIG. 2 but with the outlet valve in the open position.

Proceeding to a detailed description of one embodiment of the present invention, the pump chamber cassette 10 is shown in FIGS. 1-3 and will be utilized in conjunction with an I.V. pump shown generally at 12. The pump chamber will be supplied as an integral part of an I.V. administration set generally 11 shown in FIG. 1. The set 11 includes the usual piercing pin and drip chamber 15 interconnected to an I.V. solution or blood container 14. I.V. flexible tubing 17 interconnects drip chamber 15 with the connecting section 31 of inlet passage 28 of pump chamber 10. An additional length of flexible tubing 18 extends from tubing connection portion 72 of the outlet passage 29 of chamber 10 to needle adapter 23 for hypodermic needle 24. A support post 20 is provided to suitably support container 14 as well as I.V. pump 12.

As best seen in FIGS. 2 and 3, pump chamber unit 10 includes an intermediate housing member 26 having a cavity 27. Housing member 26 also provides an inlet passage 28 and an outlet passage 29 in fluid communication with cavity 27. The inlet passage 28 includes a connecting section 31, a chamber 32 and an intake spout 34 at the top of which is an inlet valve seat 35 and a check ball 36. A diaphragm 40 is positioned between upper housing 25 and intermediate housing 26. A projection 42 forms a portion of the diaphragm with the opposite side being substantially flat for contact with driver or plunger 45 which includes a shaft 48 terminating in a ball 47. Driver 45 is accommodated for slidable contact in guide portion 49 and has stop flanges 43 and 44 for contact with corresponding stop surfaces 38 and 39.

Disposed at the opposing end of cavity 27 is valve seat 61 against which is biased valve member 60. This biasing is effected by means of a stem 63 on valve member 60 and a stem 64 extending from support 70. A spring 65 is placed over stems 63 and 64 for the desired biasing effect. Inlet passage 28, as well as outlet passage 29 are closed by lower housing member 33 which also provides tubing connection 72.

As best seen in FIG. 3, valve seat 61 is formed from two contiguous wall sections 67 and 68. Wall section 67 is substantially parallel with the flow of liquid through the valve seat whereas wall section 68 diverges in the direction of flow. Valve member 60 is constructed with two rounded wall sections 73 and 74 which are substantially straight sided with a rounded shoulder or outwardly extending wall portion 71 therebetween.

Operation

A better understanding of the advantages of the intravenous pump chamber 10 will be had by a description of its operation.

When it is desired to administer the contents of container 14 which will have blood therein, the piercing pin and drip chamber 15 will be connected with the container and the set primed in the usual manner. Pump chamber 10 will then be placed in pump cavity 50 of pump 12 and held therein by means of support flange 30. As the flange 30 is suitably supported in the pump cavity 50, driver mechanism 46 will engage ball 47. A suitable venipuncture will then be made through hypodermic needle 22 and the pump activated by actuation such as control 52. Pump 12 will have suitable drive mechanization to move driver member 46 in an up and down motion. As driver 45 is moved toward diaphragm 40 the diaphragm will move in the direction of cavity 27 to reduce the volume thereof and force blood through the outlet passage 29 by displacement of valve member 60 to a position shown in FIG. 3. As the blood is forced past valve seat 61 it will be directed away from spring 65 and in the direction of arrows 57. This is effected by divergent wall section 68 as well as increased diameter wall section 74 of valve member 60. Not only is blood directed away from spring 65 but because of the flat wall portion 62 of valve member 60 and the divergence of wall portions 68 and 74, a low shear force will be exerted on the blood. This would not be the case where a ball type check valve such as 36 would be employed, as it has been found that a ball type valve has a tendency to move off center as it is displaced from the valve seat. This forces flow of blood through one small portion of the orifice. This, with the use of an exposed spring element, causes blood hemolysis when packed red cells are pumped through this type of an I.V. pump. These undesired effects are eliminated by the present valve outlet configuration which employs a flat wall 62 for uniform displacement of valve member 60 away from valve seat 61 as well as the divergent pathway of blood away from spring 65. This latter feature being afforded by wall portions 68 and 74.

Valve member 60 is constructed of a silicone rubber material. However, other semi-flexible materials such as natural or synthetic rubber, Kraton, or elastomeric polymers can be utilized and still obtain the benefits of this invention. Chamber housings 25, 26 and 33 are all composed of a polycarbonate material. However, other plastic materials could be employed as long as they are clear, do not contain extractables and can be readily sealed to each other as well as sealed to diaphragm 40. Diaphragm 40 is preferably fabricated from a siliconed rubber material. However, other materials such as rubber, silastic, or elastomeric polymers could be employed. While ultrasonic sealing is preferred for sealing diaphragm 40 to the respective chamber housings as well as the sealing of tubing 17 and 18 thereto, other sealing methods such as heat or mechanical means could be utilized.

It will thus be seen that through the present invention there is provided a novel pump chamber which is simple in its construction yet can be utilized to pump blood without causing hemolysis. The novel valve member and cooperating valve seat can be readily incorporated into existing pump chambers without major retooling or assembly costs.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. An intravenous pump chamber for pumping intravenous liquids including blood by means of an intravenous pump having driver means and mechanization to move the driver means in an up and down manner, said pump chamber comprising:
    a chamber defined by a housing member presenting a cavity portion;
    inlet and outlet passage means in fluid communication with said cavity;
    one way valve means operatively associated with said inlet passage means;
    a diaphragm means positioned over said cavity and spaced from said outlet passage means;
    a plunger member operatively positioned and guided to contact said diaphragm member at one end and said driver means at the other;
    said outlet passage means defined by a valve seat;
    an outlet valve member, said outlet valve member presenting a downwardly and outwardly extending lateral wall surface constructed and arranged to direct said liquid downwardly and away from said biasing means in a uniform manner as said liquid passes through said outlet passage means; and
    biasing means operatively associated with said valve member to bias said valve member against said valve seat in an axial manner.

2. The intravenous pump chamber as defined in claim 1 wherein said biasing means is a spring member and said valve member includes a stem portion to receive said spring member.

3. The intravenous pump chamber as defined in claim 2 wherein said valve member is defined by a substantially flat end surface positioned opposite said biasing means and said outwardly extending lateral wall surface is provided by a rounded shoulder portion for contact with said valve seat.

4. The intravenous pump chamber as defined in claim 3 wherein said valve member includes a straight sided wall portion positioned between said flat end surface and said rounded shoulder portion and a larger diameter circular portion presenting said wall surface directing said liquid away from said biasing means.

5. The intravenous pump chamber as defined in claim 3 wherein said valve seat is formed as an integral part of said pump chamber.

6. The intravenous pump chamber as defined in claim 5 wherein said inlet passage means includes a spout member extending away from said cavity portion.

7. The intravenous pump chamber as defined in claim 5 wherein said valve seat is defined by a portion parallel with liquid flow therethrough and a contiguous portion diverging therefrom.

8. The intravenous pump chamber as defined in claim 2 wherein said outlet passage means includes an additional stem portion to receive the opposite end section of said spring member.

9. The intravenous pump chamber as defined in claim 8 wherein said valve member is formed from a silicone rubber material.

10. The intravenous pump chamber as defined in claim 1 wherein said chamber is integrally connected to a blood administration set.

* * * * *